(12) United States Patent
Roland et al.

(10) Patent No.: US 8,699,775 B2
(45) Date of Patent: Apr. 15, 2014

(54) MAGNETIC RESONANCE SYSTEM AND METHOD TO DETERMINE AN IMAGE DATA SET THAT DESCRIBES A TEMPERATURE DISTRIBUTION IN A SUBJECT

(75) Inventors: Joerg Roland, Hemhofen (DE);
Sebastian Schmidt, Weisendorf (DE);
Anke Weissenborn, Weil am Rhein (DE)

(73) Assignee: Siemens Aktiengesellschaft, Munich (DE)

( * ) Notice: Subject to any disclaimer, the term of this patent is extended or adjusted under 35 U.S.C. 154(b) by 248 days.

(21) Appl. No.: 13/217,505

(22) Filed: Aug. 25, 2011

(65) Prior Publication Data
US 2012/0051616 A1 Mar. 1, 2012

(30) Foreign Application Priority Data
Aug. 25, 2010 (DE) .......................... 10 2010 039 737

(51) Int. Cl.
*G06K 9/00* (2006.01)

(52) U.S. Cl.
USPC ............................ 382/131; 382/128; 382/218

(58) Field of Classification Search
USPC ........................ 382/100, 128–132, 218–219
See application file for complete search history.

(56) References Cited

U.S. PATENT DOCUMENTS

| | | | |
|---|---|---|---|
| 6,559,644 B2 | 5/2003 | Froundlich et al. | |
| 7,772,846 B2 * | 8/2010 | Roland | 324/309 |
| 2008/0287773 A1 | 11/2008 | Harvey et al. | |
| 2009/0096450 A1 * | 4/2009 | Roland | 324/315 |
| 2011/0046472 A1 | 2/2011 | Schmidt et al. | |

OTHER PUBLICATIONS

"Regularized Multicoil MR Thermometry," Grisson et al. Proc. Intl. Soc. Mag. Reson. Med., vol. 17 (2009) p. 2516.
"Improved Calibration Technique for In Vivo Proton MRS Thermometry for Brain Temperature Measurement," Zhu et al., Magnetic Resonance in Medicine, vol. 60 (2008) pp. 536-541.
"Comparison of Four Magnetic Resonance Methods for Mapping Small Temperature Changes," Wlodarczyk et al., Phys. Med. Biol., vol. 44 (1999) pp. 607-624.
"Non-Invasive Temperature Imaging of Muscles with Magnetic Resonance Imaging Using Spin-Echo Sequences," Mietzsch et al., Medical and Biological Engineering and Computing (1998) pp. 673-678.
"Noninvasive Temperature Imaging Using Diffusion MRI," Delannoy et al., SMRM Workshop on Future Directions in MRI Diffusion and Microcirculation (1990) pp. 333-339.
"Absolute MR Thermometry Using Time-Domain Analysis of Multi-Gradient-Echo Magnitude Images," Sprinkhuizen et al., Magnetic Resonance in Medicine vol. 64 (2010) pp. 239-248.

* cited by examiner

*Primary Examiner* — Shefali Goradia
(74) *Attorney, Agent, or Firm* — Schiff Hardin LLP

(57) ABSTRACT

In a magnetic resonance method and apparatus to determine an examination image data set describing the temperature distribution within an examination subject (in particular a patient) using magnetic resonance an absolute temperature image data set of an examination region of the subject is acquired by magnetic resonance temperature imaging, a normal temperature data set of the examination region is determined, and the examination image data set is determined in a computerized processor by a comparison of the absolute temperature image data set with the normal temperature data set.

20 Claims, 3 Drawing Sheets

MAGNETIC RESONANCE SYSTEM AND METHOD TO DETERMINE AN IMAGE DATA SET THAT DESCRIBES A TEMPERATURE DISTRIBUTION IN A SUBJECT

BACKGROUND OF THE INVENTION

Field of the Invention

The present invention concerns: a method to generate an examination image data set describing the temperature distribution within a subject to be measured, in particular a patient, using a magnetic resonance device; as well as a magnetic resonance device for implanting such a method.

Description of the Prior Art

Methods for three-dimensional, high-resolution temperature imaging by means of magnetic resonance (magnetic resonance temperature imaging) have been known for some time. In recent years such methods have developed into a significant aid for the monitoring and control of non-invasive and minimally-invasive tumor therapy procedures.

For temperature imaging, the proton resonance frequency shift (PRF) of water protons in response to a temperature change is typically used for the temperature determination from magnetic resonance data, as is described in the article by W. Wlodarczyk et al., Phys. Med. Bio. 44, Pages 607-626, 1999, for example. Although this method is relatively robust, it has the disadvantage that only temperature changes can be measured. These temperature changes are obtained from the difference of the phase images before and during a heating process. Temperature precisions of up to 5° C. typically can be achieved with this method.

Since quite high temperature differences typically arise in tumor therapy methods, in particular greater than 10° C., magnetic resonance temperature imaging could become well established in this field in spite of the described limitations.

Due to the poor temperature precision and due to the fact that only temperature changes can be measured, conventional magnetic resonance temperature imaging has not been used in the field of diagnostics. However, in the meanwhile improved magnetic resonance sequences have been proposed and higher magnetic fields in magnetic resonance devices have been realized. A significant improvement of the temperature precision can be achieved in this way. Currently temperature changes can be measured up to a precision of 0.5° C., depending on the body region.

However, in the meanwhile reference-free methods have been proposed that enable a determination of absolute temperature image data sets. The articles by M. Zhu et al., MRM 60 (3), Pages 536-541, 2008, and W. A. Grissom et al., Abstract Nr. 2516 at the "17th International Meeting of International Society for Magnetic Resonance in Medicine (ISMRM)" are examples.

SUMMARY OF THE INVENTION

An object of invention is to provide a method to determine information about the temperature distribution within a subject to be measured, wherein the information can advantageously also be used diagnostically.

This object is achieved by a method of the aforementioned general type wherein, according to the invention an absolute temperature image data set of an examination region of the subject is acquired by magnetic resonance temperature imaging, a normal temperature data set of the examination region is determined and the examination image data set is determined in a computerized processor by a comparison of the absolute temperature image data set with the normal temperature data set.

The present invention thus enables the magnetic resonance temperature imaging to also be used increasingly for application in the diagnostic field since smaller temperature differences can be resolved. A non-invasive and spatially resolved (three-dimensional) measurement of the temperature is possible. Possible applications of magnetic resonance temperature imaging in diagnostics in which clinical pictures or disorders can be verified and analyzed based on temperature changes with the aid of magnetic resonance temperature imaging are, for example:

detection of stress-dependent temperature variations, for example due to friction, in particular (but not exclusively) within joints, for example cartilage (cartilage of the knee bones, cartilage in the patella region, for example), detection of temperature variations in or at implants (for example artificial joints, artificial or biological heart valves, artificial hearts), detection and/or documentation of chronic or acute inflammations in organs (the liver, for example) or, respectively, in the brain or in vessels as a result of plaque formation that accompany a temperature increase, temperature changes due to increased metabolism/perfusion due to tumor growth, temperature variations caused by pathologies and local inflammation reactions due to pathogens, in particular microbes, viruses or parasites, temperature variations due to acute processes such as myocardial infarction or thrombosis after taking medication, temperature variations due to chronic inflammation reactions, for example within the scope of rejection reactions, polyarthritis, general local or generalized immune reactions or possible immune disorders, local infiltration of immune cells, detection and/or control of the temperature changes given hypothermia of a patient, for example to establish and/or monitor the core temperature, detection, control and/or monitoring of the temperature variations and temperature development of a patient given targeted hypothermia of specific body parts of a patient or blood of the patient, for example within the scope of an operation, detection and control of temperature variations within the scope of burns/as a result of a burn or due to a heat accumulation, heat shock or sunstroke, detection and control of the body temperature of a fetus in the womb, of a premature child, or of an infant.

One problem of these diagnostic applications that is solved by the present invention is that a mere temperature map (ultimately thus the mere absolute temperature image data set) has only a small diagnostic value since no reference exists at all. This is true particularly in the primary fields of application of the method according to the invention, namely near the surface of the body, in particular at extremities where it cannot be assumed that the core temperature of the patient (typically 37° C.°) is uniformly present.

A local temperature rise normally occurs by locally increased perfusion, for example in case of inflammations, or can arise by supply or discharge of energy, for example by increased friction given movement or by cooling. Given a locally increased perfusion, blood with higher temperature (normally the core body temperature, thus approximately 37° C. if healthy) flows into an area of the examination region. If this region is (as already described) outside of the core of the body, for example near the skin or at an extremity, a local heating occurs.

Nevertheless, in order to determine a suitable examination image data set for a subsequent diagnosis it is consequently proposed according to the invention to determine a normal temperature data set (thus ultimately a normal temperature map) of the examination region in addition to the measured absolute temperature image data set, and to compare said normal temperature data set with the measured temperature map. The examination image data set then follows from this comparison, which examination image data set consequently offers a valuable assistance in the later diagnostic use and based on which a diagnosis can take place using the deviations from the norm. As described, this is particularly advantageous when measurements are taken in boundary regions of the subject (in particular of the patient), thus in particular near the skin and/or at extremities.

A subject image data set indicating features of the subject can additionally be acquired by means of anatomical imaging and can be taken into account in the determination of the examination image data set, or displayed together with this examination image data. In addition to an absolute temperature image data set, a subject image data set (in particular an anatomy image data set) can thus additionally be acquired, such that it is possible (for example) to also show the anatomy of the examination region together with the examination image data set, or even to enable a superimposed presentation of both image data sets so that an excellent orientation is enabled in a later diagnosis.

An intentional measure or action that affects the temperature distribution in the examination region can take place before the acquisition of the absolute temperature image data set, in particular a stressing by movement and/or an administration of medication to a patient. Corresponding measures in order to assist the accentuation of the effects of interest in a subsequent diagnosis thus can occur before acquisition of the temperature image data set. For example, a joint that is to be examined can be specifically stressed by movement, or medicines can be administered that affect the temperature, for example antipyretic agents or agents that reduce or increase perfusion.

A subject may be examined who has a body temperature that decreases toward the body surface. This applies to the human body, which typically has core a body temperature of approximately 37° C. Since this temperature frequently exists constantly inside the body (this at a distance from the skin), in an embodiment of the invention a data set indicating the core temperature in the examination area is used as a normal temperature data set for a measurement (data acquisition) inside the subject. Although temperatures increases inside the human body generally subside due to excessive perfusion or the like, pathologies and effects nevertheless are known that cause excessive temperature increases and the like inside the body, even though ultimately the core body temperature prevails in the entire examination region. For such examinations it can be assumed as a normal temperature map that the core body temperature is expected in the entire examination region.

However, as mentioned, measurements are typically made in regions in which it should not be assumed that the core body temperature or core subject temperature is uniformly present. Regions near the skin and/or examination regions at extremities of a patient are examples. In such cases the normal temperature data set is determined by measurement and/or simulation. Because the actual temperature distribution to be expected in the examination region is thus not known in principle under such circumstances, the distribution is measured and/or to simulated in order to obtain the normal temperature data set (thus the normal temperature map) as a result. Different variants to obtain a normal temperature data set are conceivable, partially dependent on the examination to be implemented and the examination region.

In an embodiment of the invention, in order to determine the normal temperature data set given the acquisition of data from a mirror-reversed examination region in a subject (in particular an extremity of a patient), the physically opposite counterpart of the examination region is acquired and mirrored. For example, in the case of a laterally symmetric organ system, for example an extremity exhibiting lateral symmetry, the opposite side can be measured, for example the left knee in comparison to the examined right knee (which forms the examination region from which the diagnostic image data are to be acquired). A comparison is possible when a mirroring is produced due to the symmetry of the occurrence in the examination region, which means that the image data set of the opposite side that is acquired by means of magnetic resonance temperature imaging is mirrored so that it corresponds in terms of its alignment to the examination region. It is then possible to make a comparison between the normal temperature data set determined in such a manner and the absolute temperature data set of the examination region. It is also possible to implement an elastic registration of the mirrored image data set and the absolute temperature data set. A transformation thus can be applied in order to enable the comparison of the temperature maps. For example, such a procedure is known from DE 10 2005 052 993 A1. Although these are anatomical evaluations, the method described therein can also be used in the context according to the invention. A deformation is initially implemented so that two halves that are mirror-symmetrical with regard to their shape are present which can then be compared to determine differences.

In a further embodiment that is useful for the measurement of a temporary temperature variation (in particular a temperature variation following a measure to intentionally vary the temperature distribution in the examination region), an image data set, for use as a normal temperature data set, is acquired at a point in time before the temperature variation or after the temperature variation. In the case of a temporary effect, for example a heating that occurs only under stress, the normal temperature data set can be measured at a different point in time from the absolute temperature data set. For example, the absolute temperature map can be initially measured after stressing a joint, after which an additional magnetic resonance temperature measurement is implemented later, after a duration to permit cooling, in order to acquire the normal temperature data set. A measurement (acquisition) of the normal temperature data set after the absolute temperature data set is therefore advantageous because the patient must be moved into the magnetic resonance device only a single time. In this context, a measurement is repeated until the temperature no longer changes, indicating that this (last) measurement can then be used as a normal temperature map (normal temperature data set).

In a further embodiment, the normal temperature data set is determined from a simulation that takes into account variables affecting the temperature distribution in the examination region, in particular heat sources, heat sinks and/or the heat conductivity of regions situated between heat sources and/or heat sinks. It is also possible for a normal temperature data set to be simulated using the significant influencing variables. For example, in the case of the human body, the significant heat sources, heat losses and the heat conductivity of the intervening tissue are taken into account. For example, arteries and/or muscle tissue as heat sources, and/or the skin surface and/or veins as heat sinks, and/or (as an additional variable) the heat conductivity of the intervening tissue can be used as in a measurement of a patient as the examination subject. The arteries for the most part supply blood at the core body temperature while (for example in the case of a leg) the veins transporting the blood returning from the toes can be cooler. Furthermore, heat is emitted at the skin surface, while the muscle tissue in which oxidation takes place is present as an additional heat source. In this context it is possible for the blood flow in the examination region to be measured using known techniques for magnetic resonance blood flow measurement, and/or for muscle tissue and adipose tissue in the target region to be segmented in a method to separate muscle tissue and adipose tissue in the magnetic resonance. Ultimately, it can be determined by means of a magnetic resonance blood flow measurement how much blood (thus heat) is transported into the examination region. Angiographic sequences are known for this purpose, in which labeling methods can also be used in which an excitation slice and a measurement slice can be considered. In principle, in magnetic resonance measurement it is also known to differentiate muscle tissue and aqueous tissue. While muscle tissue contains more water, adipose tissue consists primarily of fat, such that spectral methods can be used for separation, for example, but phase differences can also be considered. The muscle tissue can then be viewed as a heat source; the adipose tissue forms a manner of "insulation".

Furthermore, within the scope of the simulation it can be appropriate for a core temperature of the subject to be measured (in particular by means of a separate magnetic resonance temperature measurement) and/or to measure an external temperature of the subject (in particular by means of a thermometer integrated into the magnetic resonance device) and to take such measurement results into account in the simulation. While it can naturally also be possible (and frequently even sufficient) in principle to estimate the core temperature (in particular the core body temperature) and/or the external temperature (in particular the temperature at the skin surface), it can be advantageous to measure at least one of the two variables. A thermometer (in particular an infrared thermometer) integrated into the magnetic resonance device can be used, which can measure the temperature at the skin surface.

In principle, thermodynamic simulation methods that output a temperature map about known heat sources, heat sinks and heat conductivities are widely known and do not need to be described in detail herein. However, for explanatory assistance an exemplary procedure is described within the scope of the determination of a normal temperature data set via simulation. If a leg is considered as the target region, aside from the absolute temperature distribution the blood flow in the femoral artery (or internal iliac artery), the distribution of the muscle tissue (as a heat source) and adipose tissue (as "insulation") can also be determined during the magnetic resonance examination. The tissue can simply be segmented separately using techniques for fat-water separation. Furthermore, the core body temperature is determined (or assumed) at 37° C., and the skin temperature is measured or estimated. From such measurement data a model is automatically created that reproduces the heat flows through the different slices and that simulates a temperature distribution that can then be used as a normal temperature data set.

Within the scope of the comparison, the examination data set may be determined by subtraction of the normal temperature data set from the absolute temperature data set. The difference of the two data sets is thus considered so that the locations at which deviations from the "norm" occur are emphasized, such that a simple interpretation of the examination data set is possible in a diagnosis following the method according the invention.

More specifically, in a presentation of the examination image data set the examination image data set, determined by subtraction of the normal temperature data set from the absolute temperature data set, temperature deviations can be shown by a false color presentation or by isothermal lines. Such false color presentations are known in principle. A specific color is thereby associated with a specific region in which the temperatures (temperature range) deviate. For example, a red color scale can be used for regions that are warmer than indicated by the normal temperature data set, and a blue color scale is used for regions that are cooler than indicated by the normal temperature data set. It is also possible to represent the examination image data set by means of isothermal lines. The points at which specific, identical values of a temperature deviation are present are thereby emphasized as a line so that an image that can be clearly interpreted likewise results.

In addition to the method, the present invention also encompasses a magnetic resonance apparatus having a control device fashioned to operate a magnetic resonance data acquisition device (scanner) in order to implement the method according to the invention. The control device is thus fashioned (configured) not only to acquire an absolute temperature image data set by means of a suitable sequence for magnetic resonance temperature imaging, but also to determine a normal temperature data set (in particular via measurement and/or by simulation) that is then compared with the absolute temperature image data set to determine an examination image data set so that ultimately temperature deviations from the norm can be presented. The method and apparatus according to the invention thus make magnetic resonance temperature imaging, specifically in regions near the skin and at extremities, accessible to the diagnostic field by providing a tool for preparing a diagnosis as well as an advantageous procedure for the examination of subjects other than patients.

All statements above with regard to the method according to the invention are analogously applicable to the magnetic resonance device according to the invention.

The magnetic resonance apparatus can include an integrated thermometer, in particular an infrared thermometer. It is therefore advantageously made possible to measure the surface temperature of the skin of a patient with the magnetic resonance device itself, so that it is advantageously possible to use the corresponding measurement values in a simulation to determine the normal temperature data set, for example.

DESCRIPTION OF THE PREFERRED EMBODIMENTS

Figure 1:
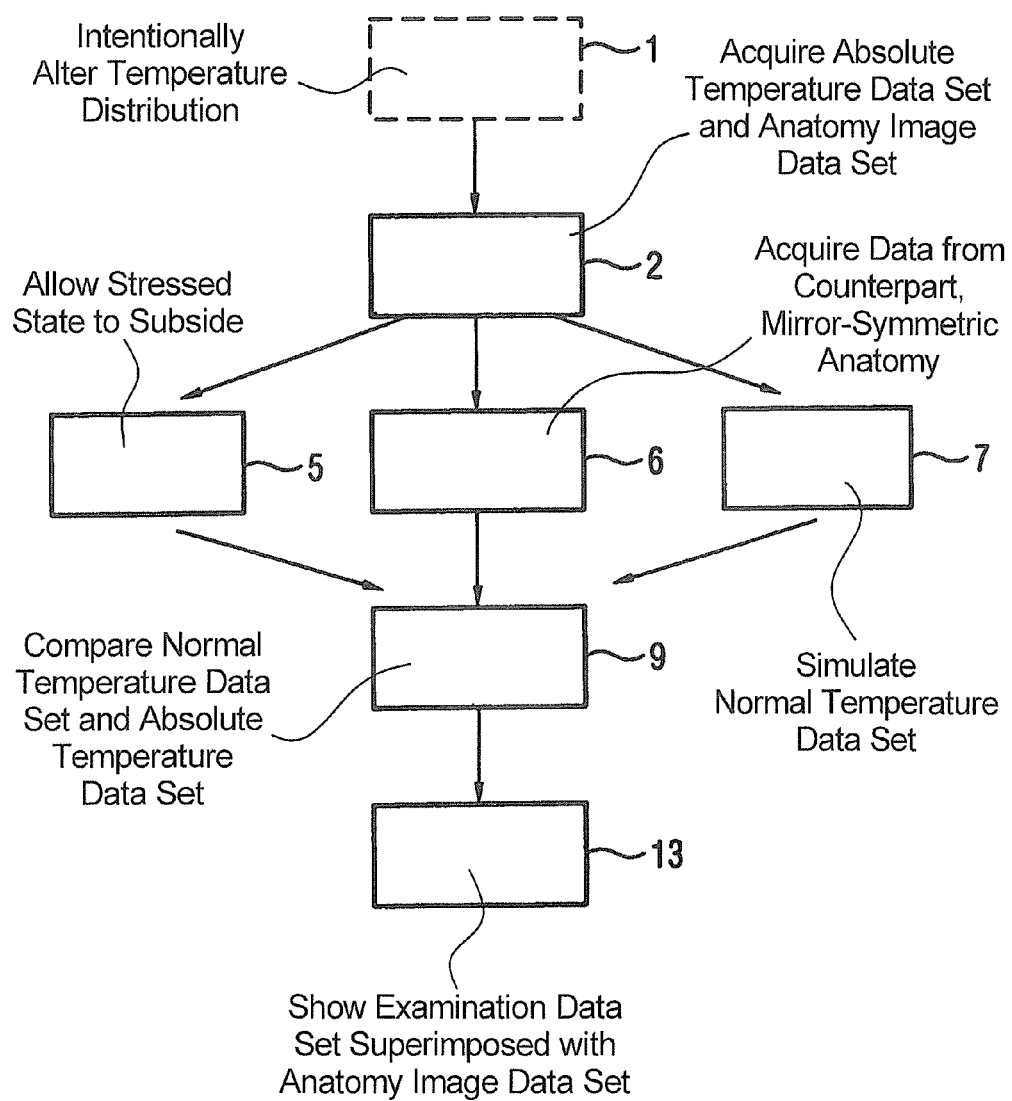
FIG. 1 is a basic flowchart of an embodiment of the method according to the invention.

FIG. 1 shows a flowchart of an embodiment of the method according to the invention. The method according to the invention serves to procure an examination image data set that, in the exemplary embodiment (but naturally not limited to this), should show temperature deviations in the knee of a patient.

For this purpose, in an optional Step 1 a measure or action (altering) affecting the temperature distribution in the examination region can take place. In this embodiment, this measure is a stressing by movement of the knee. As soon as a certain stress is present, the patient is positioned as quickly as possible within the magnetic resonance device in order to take the exposures.

Figure 2:
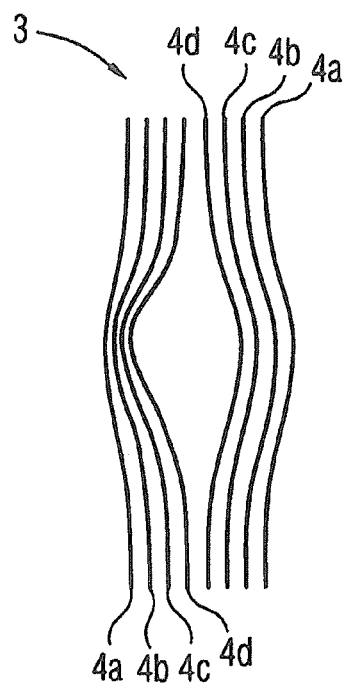
FIG. 2 illustrates an absolute temperature data set obtained in accordance with the invention.

In Step 2, two image data sets are acquired, namely an absolute temperature image data set by means of magnetic resonance temperature imaging and an anatomy image data set by means of anatomical imaging. The absolute temperature image data set shows the absolute temperatures in the examination region (thus here the knee) and, the anatomy image data set shows the anatomy of the knee. FIG. 2 shows an example of such an absolute temperature image data set 3. This is characterized by isotherms 4a through 4d, wherein the isotherm 4a corresponds to a temperature of 31°; the isotherm 4b corresponds to a temperature of 33°; the isotherm 4c corresponds to a temperature of 35°; and the isotherm 4d corresponds to a temperature of 37°.

In order to be able to prepare a diagnosis following the method according to the invention, however, information is now required about how the temperature distribution normally appears in the knee; a normal temperature data set (normal temperature map) must consequently be determined. For this purpose, in the method according to the invention three possibilities ultimately also exist in this exemplary embodiment, which possibilities are indicated altogether as options in FIG. 1.

In method Step 5 it can be provided as a first alternative to leave the patient in the magnetic resonance device until the stress state of the knee has dissipated (subsided). For this purpose, to acquire additional image data sets can be acquired by means of magnetic resonance temperature imaging at regular time intervals until variation no longer occurs, thus until the unstressed state is achieved. The corresponding data can then be used as a normal temperature data set of the examination region (thus of the knee).

In a second alternative, in Step 6, data from the other knee (thus the counterpart to the examination region) is acquired, in particular simultaneously with the knee to be examined (thus the examination region), when it can be assumed that this knee is either not stressed or that the effect that are to be observed does not occur there. Two image data sets are consequently then present, namely the absolute temperature image data set of the actual examination region and that of the symmetrical existing opposite side. In particular, an anatomical image data set can be acquired for both knees, and the anatomical image data sets can then be elastically registered with one another, which transformation can then also be transferred to the temperature image data sets acquired by means of magnetic resonance temperature imaging. The normal temperature data set can then be obtained by a simple mirroring of the knee to be examined before or after the described elastic registration.

It is naturally also possible in principle to achieve an elastic registration by means of the temperature image data sets, wherein then only the regions in which no extreme deviations are expected should be considered.

In the third alternative (method Step 7) the normal temperature data set is determined via simulation. For this, apart from the temperature distribution and the anatomical features the blood flow in the femoral artery (or internal iliac artery), the distribution of the muscle tissue (as a heat source) and adipose tissue (as "insulation") are also initially determined during the magnetic resonance examination. The tissue types can simply be segmented by techniques for fat-water separation. Furthermore, the core body temperature is either determined (via separate measurement, for example) or assumed as 37° C. The skin temperature can be estimated or (preferably) measured by a contact-less thermometer (in particular an infrared thermometer) integrated into the magnetic resonance device. A model that reproduces the heat flows through the different slices and simulates a temperature distribution that can then be used as a normal temperature data set is now generated entirely automatically from these measurement data and measurement data sets.

Figure 3:
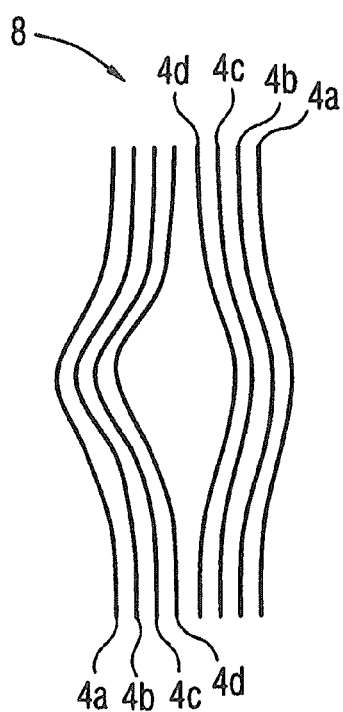
FIG. 3 illustrates a normal temperature data set obtained in accordance with the invention.
Figure 4:
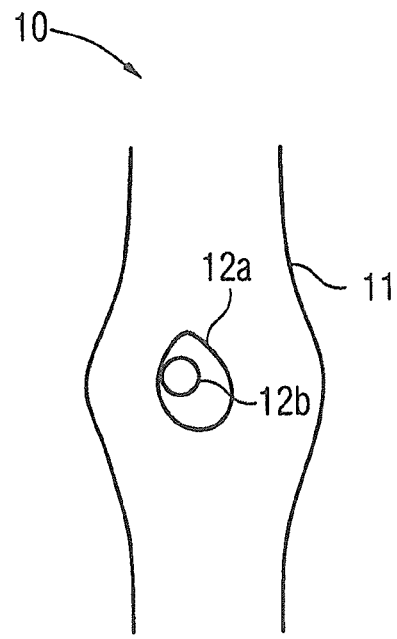
FIG. 4 illustrates an examination image data set obtained in accordance with the invention.

A normal temperature data set that can be obtained in the method Step 5, 6 or 7 is presented as an example in FIG. 3, wherein the temperature distribution is in turn depicted via isotherms 4a-4d. The comparison between the absolute temperature data set 3 and the normal temperature data set 8 then takes place in Step 9 in that the normal temperature data set 8 is subtracted from the absolute temperature image data set 3 in order to obtain an examination image data set 10 as it is shown as an example in FIG. 4. For clarification, the boundary lines of the anatomy are still indicated at 11. In the final presentation this can be achieved in that the anatomy image data set is superimposed on the examination image data set. Isotherms 12a and 12b clearly identify a temperature deviation region, wherein the isotherm 12a corresponds to a temperature difference of 1° and the isotherm 12b corresponds to a temperature difference of 2° C.

In Step 13 the examination image data set 10 is then shown superimposed with the anatomy image data set so that where a difference (possibly a lesion) is present can easily be recognized in a subsequent diagnosis process.

The presentation does not need to take place in the form of isothermal lines; rather, a false color presentation can also advantageously be used, for example. For example, temperatures exceeding the normal temperature can thereby be shown in a red color scale; temperatures falling below the normal temperature can be shown in a blue color scale.

Figure 5:
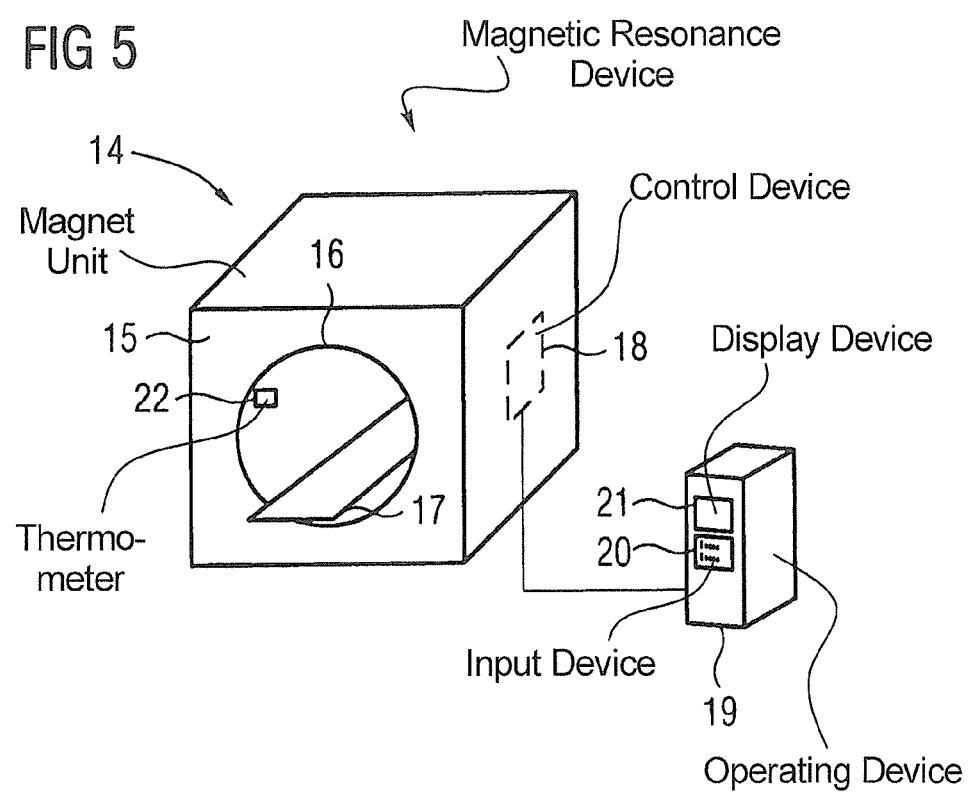
FIG. 5 schematically shows a magnetic resonance device according to the invention.

FIG. 5 shows a schematic illustration of a magnetic resonance device 14 according to the invention. As is generally known, this includes a basic magnet unit 15 (data acquisition unit) at which the gradient coils, the radio-frequency coils and the like are also provided. All of these do not need to be shown in detail herein since they are fundamentally known to those skilled in the art. A patient can be driven into a patient receptacle 16 by means of a patient bed 17. The operation of the magnetic resonance device 14 is controlled by a control device 18 that is also fashioned to implement the method according to the invention. Also belonging to the magnetic resonance device 14 are an operating device 19 (console) with an input device 20 and a display device 21, for example one or more monitors that can also serve for presentation of the examination image data set 10 superimposed with the anatomy image data set.

In the magnetic resonance device 15 according to the invention, an infrared thermometer 22 with which in particular the surface temperature of a subject to be examined (in particular the skin temperature of a patient) can be measured can be integrated within the patient receptacle 16. This can advantageously provide data that enter into the simulation to determine the normal temperature data set in Step 7.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to determine an examination image data set that describes a temperature distribution within a subject, comprising the steps of:
    operating a magnetic resonance data acquisition unit, in which a subject is located, to obtain an absolute temperature image data set, by magnetic resonance temperature imaging, of an examination region of the subject;
    generating a normal temperature data set of the examination region of the subject;
    in a computerized processor, comparing the absolute temperature image data set with said normal temperature data set to obtain an examination image data set;
    operating said magnetic resonance data acquisition unit to additionally acquire a subject image data set from the subject that shows physical characteristics of the subject;
    in said computerized processor, reconstructing an examination image from said examination image data set and reconstructing a subject image from said subject image data set; and
    from said computerized processor, causing simultaneous display, at a display screen, of said examination image and said subject image.

2. A method as claimed in claim 1 comprising reconstructing said examination image data set additionally using said subject image data set.

3. A method as claimed in claim 1 wherein said subject is a patient, and wherein said patient exhibits a core temperature that decreases toward a surface of the subject.

4. A method as claimed in claim 3 comprising using, as said normal temperature data set, a data set that indicates the core temperature in the examination region, obtained by making a measurement of said core temperature inside of the patient, other than by said magnetic resonance temperature imaging.

5. A method as claimed in claim 1 comprising determining said normal temperature data set by making a temperature measurement of the subject, other than by said magnetic resonance temperature imaging.

6. A method as claimed in claim 1 comprising determining said normal temperature data set by implementing a computerized simulation of at least said examination region of said subject.

7. A method as claimed in claim 1 wherein said subject comprises a counterpart region that is mirror-symmetric with respect to said examination region, and comprising determining said normal temperature data set by implementing mirror-reversed magnetic resonance temperature imaging of said counterpart region, to obtain a mirror-reversed data set, and mirroring said mirror-reversed data set.

8. A method as claimed in claim 7 comprising implementing an elastic registration to bring said mirrored, mirror-reversed data set into registration with said absolute temperature data set.

9. A method as claimed in claim 1 comprising determining said normal temperature data set by intentionally inducing a temporary temperature variation in said examination region and acquiring said normal temperature data set by magnetic resonance temperature imaging implemented at a point in time selected from the group consisting of before said temperature variation and after said temperature variation.

10. A method as claimed in claim 1 comprising determining said normal temperature data set by implementing a simulation algorithm that simulates a temperature distribution at least in said examination region, using variables that affect said temperature distribution selected from the group consisting of heat sources, heat sinks, and heat conductivity in portions of said examination region situated between heat sources, heat conductivity of regions situated in said examination region between heat sinks, and heat conductivity of regions in said examination region situated between at least one heat source and at least one heat sink.

11. A method as claimed in claim 10 wherein the subject is a patient, and comprising using at least one of arteries and muscle tissue as heat sources, and using a skin surface and veins as heat sinks, and using heat conductivity of intervening tissue between at least one heat source and one heat sink as said heat conductivity of said portion of said examination region.

12. A method as claimed in claim 11 comprising measuring blood flow in said examination region using a magnetic resonance blood flow measurement procedure, and embodying said blood flow in said simulation algorithm.

13. A method as claimed in claim 12 comprising generating a magnetic resonance image of the examination region that shows muscle tissue and adipose tissue, and segmenting said muscle tissue and said adipose tissue and using the segmented muscle tissue and adipose tissue in said simulation.

14. A method as claimed in claim 10 comprising making a core temperature measurement of the subject by a separate magnetic resonance temperature measurement and, in said processor, using said core temperature measurement in said simulation.

15. A method as claimed in claim 10 comprising making an external temperature measurement of the subject using a thermometer integrated into said magnetic resonance data acquisition device, and using said external temperature measurement in said simulation.

16. A method as claimed in claim 1 comprising generating said examination image data set by subtracting said normal data set from said absolute temperature data set.

17. A method as claimed in claim 1 wherein said examination data set comprises temperature deviations, and comprising, from said processor, causing said examination image data set to be visually displayed with visual indications of said temperature deviations, selected from the group consisting of false color presentation and isothermal lines.

18. A magnetic resonance system for determining an examination image data set that describes a temperature distribution within a subject, said system comprising:
    a magnetic resonance data acquisition unit;
    a control unit configured to operate said magnetic resonance data acquisition unit, with a subject located therein, to obtain an absolute temperature image data set, by magnetic resonance temperature imaging, of an examination region of the subject;
    a computerized processor provided with a normal temperature data set of the examination region of the subject;
    a display unit in communication with said computerized processor;
    said computerized processor being configured to compare the absolute temperature image data set with said normal temperature data set to obtain an examination image data set;
    said control unit being configured to operate said magnetic resonance data acquisition unit to additionally acquire a subject image data set from the subject that shows physical characteristics of the subject;
    said computerized processor being configured to reconstruct an examination image from said examination image data set and to reconstruct a subject image from said subject image data set; and said computerized processor being configured to cause simultaneous display of said examination image and said subject image at said display unit.

19. A method to determine an examination image data set that describes a temperature distribution within a subject, comprising the steps of:

intentionally implementing a measure that affects a temperature distribution in an examination region of a subject;

after intentionally implementing said measure that affects said temperature distribution, operating a magnetic resonance data acquisition unit, in which the subject is located, to obtain an absolute temperature image data set, by magnetic resonance imaging, of the examination region of the subject;

generating a normal temperature data set of the examination region of the subject; and in a computerized processor, comparing the absolute temperature image data set with said normal temperature data set to obtain an examination image data set, and making said examination image data set available as a data file at an output of said processor.

20. A method as claimed in claim 19 comprising selecting said measure from the group consisting of stressing said examination region by physical movement thereof, and administration of a medication to the subject.

* * * * *